US011155635B2

(12) United States Patent
Yoon et al.

(10) Patent No.: US 11,155,635 B2
(45) Date of Patent: Oct. 26, 2021

(54) ANTI-COAGULATION FACTOR VIII ANTIBODY AND USE THEREOF

(71) Applicant: PANGEN BIOTECH INC., Gyeonggi-do (KR)

(72) Inventors: Jaeseung Yoon, Gyeonggi-do (KR); Kwanghee Baek, Gyeonggi-do (KR); Taeho Byun, Gyeonggi-do (KR); Jeong Soo Park, Gyeonggi-do (KR); Ji Tai Kim, Gyeonggi-do (KR); Hankyu Oh, Gyeonggi-do (KR); Jongmin Lee, Seoul (KR)

(73) Assignee: PANGEN BIOTECH INC., Gyeonggi-Do (KR)

( * ) Notice: Subject to any disclaimer, the term of this patent is extended or adjusted under 35 U.S.C. 154(b) by 290 days.

(21) Appl. No.: 16/464,287

(22) PCT Filed: Dec. 14, 2017

(86) PCT No.: PCT/KR2017/014747
§ 371 (c)(1),
(2) Date: May 27, 2019

(87) PCT Pub. No.: WO2018/111010
PCT Pub. Date: Jun. 21, 2018

(65) Prior Publication Data
US 2020/0277401 A1     Sep. 3, 2020

(30) Foreign Application Priority Data

Dec. 14, 2016 (KR) .................. 10-2016-0170646
Dec. 14, 2017 (KR) .................. 10-2017-0171867

(51) Int. Cl.
*C07K 16/36* (2006.01)
*C07K 1/16* (2006.01)
*C07K 14/755* (2006.01)

(52) U.S. Cl.
CPC ............ *C07K 16/36* (2013.01); *C07K 1/16* (2013.01); *C07K 14/755* (2013.01); *C07K 2317/565* (2013.01); *C07K 2317/567* (2013.01)

(58) Field of Classification Search
None
See application file for complete search history.

(56) References Cited

U.S. PATENT DOCUMENTS 4,361,509 A * 11/1982 Zimmerman ............. A61P 7/04
                                                      530/383
6,180,370 B1 * 1/2001 Queen ................ C07K 16/2866
                                                       435/69.6

FOREIGN PATENT DOCUMENTS

| EP | 0317279 A2 * | 5/1989 | ........... C07K 14/755 |
|---|---|---|---|
| JP | 2009502149 A | 1/2009 | |
| KR | 100245542 B1 | 2/2000 | |
| KR | 100254574 B1 | 5/2000 | |
| KR | 1020030029128 A | 5/2003 | |
| WO | WO2013098676 A1 | 7/2013 | |
| WO | WO-2014201400 A2 * | 12/2014 | ............. C07K 16/36 |

OTHER PUBLICATIONS

Lescar, et al. Journal of Biological Chemistry 270.30 (1995): 18067-18076.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Kanyavuz et al., Nat Rev Immunol. Jun. 2019;19(6):355-368. doi: 10.1038/S41577-019-0126-7.*
Kipriyanov et al., Mol Biotechnol. Jan. 2004;26(1):39-60. doi: 10.1385/MB:26:1:39.*
Mishra, N., et al., "Antibodies to major histocompatibility antigens produced by hybrid cell lines", "Nature", Apr. 1977, pp. 550-552, vol. 266, Publisher: Nature Publishing Group.

* cited by examiner

*Primary Examiner* — Michael Szperka
(74) *Attorney, Agent, or Firm* — Hultquist, PLLC; Steven J. Hultquist

(57) ABSTRACT

The present invention relates to an antibody specifically bound to a coagulation factor VIII or an antigen binding fragment thereof, and a use thereof. More specifically, the present invention relates to: an antibody which is specifically bound to a coagulation factor VIII including specific sequences of heavy chain CDR and light chain CDR, or an antigen binding fragment thereof; a column in which the antibody or the antigen binding fragment thereof is coupled to a column stationary phase as a ligand for isolating or purifying a recombinant coagulation factor VIII; and a method for purifying a recombinant coagulation factor VIII using the same.

10 Claims, 3 Drawing Sheets

Specification includes a Sequence Listing.

Lane 1. Blank
Lane 2. Blank
Lane 3. Marker
Lane 4. Purified antibody protein (1 μg)
Lane 5. Purified antibody protein (3 μg)
Lane 6. Purified antibody protein (5 μg)
Lane 7. Blank
Lane 8. Marker
Lane 9. Blank
Lane 10. Purified antibody protein (1 μg)
Lane 11. Purified antibody protein (3 μg)
Lane 12. Purified antibody protein (5 μg)

Lane 1. Blank
Lane 2. Marker
Lane 3. Blank
Lane 4. Factor VIII (200 ng)
Lane 5. Factor VIII (400 ng)
Lane 6. Blank

ANTI-COAGULATION FACTOR VIII ANTIBODY AND USE THEREOF

CROSS-REFERENCE TO RELATED APPLICATIONS

This is a U.S. national phase under the provisions of 35 U.S.C. § 371 of International Patent Application No. PCT/KR17/14747 filed Dec. 14, 2017, which in turn claims priority of Korean Patent Application No. 10-2016-0170646 filed Dec. 14, 2016 and Korean Patent Application No. 10-2017-0171867 filed Dec. 14, 2017. The disclosures of such international patent application and Korean priority patent applications are hereby incorporated herein by reference in their respective entireties, for all purposes.

TECHNICAL FIELD

The present invention relates to an antibody binding specifically to a coagulation factor VIII or an antigen-binding fragment thereof, and to the use thereof. More specifically, the present invention relates to an antibody specifically binding to a coagulation factor VIII or an antigen-binding fragment thereof, which includes a heavy chain CDR and a light chain CDR, each having a specific sequence, a column for purifying a recombinant coagulation factor VIII, to which the antibody or an antigen-binding fragment thereof is coupled, and a method for isolating or purifying a recombinant coagulation factor VIII using the same.

BACKGROUND ART

Hemocoagulation (blood clotting) is conducted using a process of forming stabilized (cross-linked) fibrin through a coagulation cascade of various constituent components such as coagulation factor I (fibrinogen) as well as coagulation factors II, III, V, VII, VIII, IX, X, XI, XII and XIII (the Roman numeral of the coagulation factor does not indicate the order of the sequential reaction). When even one of these coagulation factors is deficient, bleeding will occur in the human body due to unfavorable hemocoagulation. Symptoms that can be clinically observed due to such hemocoagulation disorders include joint deformities due to intraarticular hemorrhaging, edema due to intramuscular hemorrhaging, and intracranial hemorrhaging. Excessive hemorrhaging (bleeding) can lead to life-threatening symptoms.

Hemophilia, which is a representative hemocoagulation disorder, is a genetic X-linked recessive disorder and is rarely caused by mutations. Hemophilia is classified into Type A hemophilia, caused by deficiency of coagulation factor VIII (FVII), and Type B hemophilia, caused by deficiency of coagulation factor IX (FIX). In addition, hemophilia can be classified into mild, moderate and severe hemophilia depending on the degree of deficiency of the relevant coagulation factor. It is estimated that Type A hemophilia occurs in about 1 in 5,000 male births and Type B hemophilia occurs in about 1 in 20,000 male births, and there are at least 400,000 hemophilia patients worldwide. Methods for externally administering deficient coagulation factors for the on-demand and prophylactic treatment of hemophilia have been used. The replacement therapy of deficient coagulation factors can prolong the life expectancy of hemophilia patients.

For half a century, coagulation factor VIII has been concentrated, separated and purified from the plasma of normal people and has been used for the treatment of Type A hemophilia. However, the risk of infections with hemorrhagic viruses such as HIV and hepatitis viruses (Type B and C) caused by the administration of plasma-derived drugs started to arise in the early 1980s. For this reason, the use of recombinant coagulation factor VIII, which eliminates the risk of hemorrhagic viral infections, has gradually increased since 1988.

Isolation and purification of the recombinant coagulation factor VIII are carried out through a series of chromatographic steps like common processes for separating and purifying protein therapeutics. Chromatography is a method of separating a target substance using two mutually immiscible phases, for example, by bringing a mobile phase in which the target substance to be separated is dissolved together with various substances into contact with another phase, that is, a stationary phase. A sample mixture, which is dissolved in the mobile phase, undergoes a series of interactions with the stationary phase while the mobile phase flows through a column filled with the stationary phase. The behavior of such interaction depends on the physical or chemical properties of the ingredients (solutes) of the sample mixture. The difference in the properties of each constituent component causes a difference in interaction strength with the stationary phase and consequently leads to a difference in the migration rate of each solute under the influence of the composition of the mobile phase flowing through the column filled with the stationary phase. Each solute separated depending on the composition of the mobile phase and the flow rate is eluted in the reverse order of strength of interaction with the stationary phase. The solute that is most weakly retained in the stationary phase is first eluted from the column, and the solute that is the most strongly retained in the stationary phase is finally eluted. When, during elution of sample components, separation of components is unfavorable since the elution time of one component (solute) is similar to the elution time of another component (solute) from the column, the difference in elution time between the components can be made sufficiently long through changes in chromatographic conditions (stationary phase and/or mobile phase) in order to separate the components as desired. Therefore, a stationary phase satisfying optimal conditions for separation of each specific component is required, and efforts to design the same are continuously being made. The above-described stationary phase generally consists of a support or matrix, to which a ligand including a functional group, i.e., a linking group, is attached. Chromatography can be characterized into various types of chromatography, each based on the principle of interaction of sample components in used stationary and mobile phases. Examples of such chromatography include ion exchange chromatography, hydropathic interaction chromatography, and affinity chromatography.

Among them, affinity chromatography is based on the specific interaction between the target biomolecule and the biospecific ligand, according to the principle of lock and key recognition. Thus, the target and the ligand consist of an affinity pair, such as an antigen/antibody, an enzyme/substrate, and a ligand/receptor. Protein A, protein G and the like are well-known as ligands for protein-based affinity chromatography, which is a method that is widely used for the separation and purification of proteins. It is well-known that protein A chromatography in particular provides notable specificity for monoclonal antibodies, and consequently is capable of being used to obtain monoclonal antibodies with high purity.

Under these technical background, the inventors of the present application have developed a novel antibody specifically binding to a coagulation factor VIII, and have found that a recombinant coagulation factor VIII can be purified at high purity by applying the antibody to the purification of recombinant coagulation factor VIII. Based on this finding, the present invention has been completed.

DISCLOSURE

Technical Problem

Therefore, the present invention has been made in view of the above problems, and it is one object of the present invention to provide a novel antibody binding specifically to a coagulation factor VIII or an antigen-binding fragment thereof.

It is another object of the present invention to provide a polynucleotide encoding the antibody or antigen-binding fragment thereof, a recombinant expression vector including the same, a host cell including the same and a method of producing the antibody.

It is another object of the present invention to provide a column for purifying a recombinant coagulation factor VIII, to which the antibody or antigen-binding fragment thereof binds, and a method for isolating or purifying a recombinant coagulation factor VIII using the same.

Technical Solution

In accordance with the present invention, the above and other objects can be accomplished by the provision of an antibody binding specifically to a coagulation factor VIII, or an antigen-binding fragment thereof including: a heavy chain CDR selected from the group consisting of SEQ ID NO: 1, SEQ ID NO: 2, and Tyr His Phe; and a light chain CDR selected from the group consisting of SEQ ID NOS: 3 to 5.

In accordance with another aspect of the present invention, provided is a polynucleotide encoding the antibody or an antigen-binding fragment thereof.

In accordance with another aspect of the present invention, provided is a recombinant expression vector including the polynucleotide.

In accordance with another aspect of the present invention, provided is a host cell transformed with the recombinant expression vector.

In accordance with another aspect of the present invention, provided is a method of producing an antibody including culturing the host cell to produce an antibody or an antigen-binding fragment thereof and recovering the produced antibody or antigen-binding fragment thereof, followed by isolation and purification.

In accordance with another aspect of the present invention, provided is a column for isolating or purifying a recombinant coagulation factor VIII, to which the antibody or antigen-binding fragment thereof is coupled.

In accordance with another aspect of the present invention, provided is a method of purifying the recombinant coagulation factor VIII including loading a sample containing a recombinant coagulation factor VIII on the column.

Other technical features and embodiments of the present invention will be more clearly described in the following Detailed Description of the Invention and Claims set forth later.

BRIEF DESCRIPTION OF THE DRAWINGS

The above and other objects, features and other advantages of the present invention will be more clearly understood from the following detailed description taken in conjunction with the accompanying drawings, in which.

BEST MODE

Figure 1:
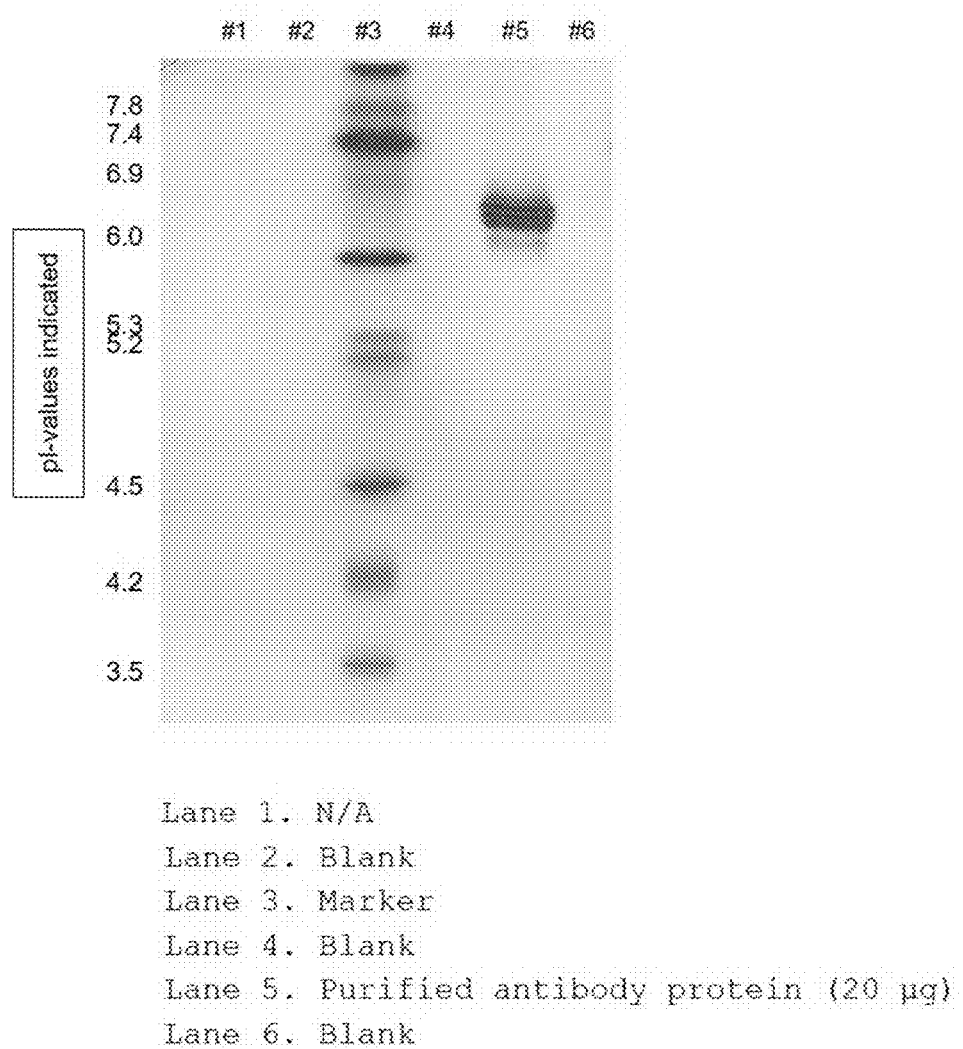
FIG. 1 shows the result of identifying the isoelectric point of an antibody by separating a purified antibody protein based on an isoelectric point.

In one aspect, the present invention is directed to an antibody binding specifically to a coagulation factor VIII or an antigen-binding fragment thereof including: a heavy chain CDR selected from the group consisting of SEQ ID NO: 1, SEQ ID NO: 2, and Tyr His Phe; and a light chain CDR selected from the group consisting of SEQ ID NOS: 3 to 5.

The term "antibody" as used herein means a protein molecule including an immunoglobulin molecule that specifically recognizes an antigen and thus immunologically reacts with the specific antigen, and includes a whole antibody binding specifically to a coagulation factor VIII as well as an antigen-binding fragment of the antibody molecule.

The whole antibody is composed of two full-length light chains and two full-length heavy chains, wherein each light chain is linked to a heavy chain by a disulfide bond. In mammals, five antibody isotypes, known as IgA, IgD, IgE, IgM, and IgG, exist and IgG is further classified into the four antibody subtypes IgG1, IgG2, IgG3 and IgG4.

The term "antibody fragment" as used herein refers to a minimal fragment that maintains an antigen-binding ability and includes Fab, F(ab'), F(ab')$_2$, and Fv. Fab includes a variable region of each of the heavy chain and the light chain, the constant domain of the light chain, and the first constant domain (CH1) of the heavy chain, each having an antigen-binding site. Fab' is different from Fab in that it further includes at least one cysteine residue at a C-terminus of the CH1 domain of the heavy chain. F(ab')$_2$ includes two Fab' molecules having a disulfide bond between cysteine residues in a hinge region. An Fv (variable fragment) including a variable region of each of the heavy chain and the light chain is the minimal antibody fragment having original specificity for the parent immunoglobulin. Disulfide-stabilized Fv (dsFv) is formed by binding the variable region of the light chain to the variable region of the heavy chain via a disulfide bond. Single-chain Fv (scFV) is an Fv where the respective variable regions of the heavy chain and the light chain are covalently linked via a peptide linker. These antibody fragments can be obtained by treating the whole antibody with a protease (for example, papain or pepsin providing Fab or F(ab')$_2$), and are preferably constructed using genetic recombination technology.

In one embodiment, the antibody according to the present invention is a FV (for example, scFV) or complete antibody type. In addition, the heavy-chain constant region may be selected from γ, μ, α, δ and ε isotypes. The light-chain constant region may be a κ or λ type.

The term "heavy chain" as used herein may be interpreted to include a full-length heavy chain including a variable region domain VH including an amino acid sequence having a variable region sequence sufficient to impart specificity to an antigen and three constant region domains CH1, CH2 and CH3 and a fragment thereof. Also, the term "light chain" as used herein may be interpreted to include a full-length light chain including a variable region domain VL including an amino acid sequence having a variable region sequence sufficient to impart specificity to an antigen and a constant region domain CL and a fragment thereof.

In general, immunoglobulin has a basic structural unit including two heavy chains and two light chains. Each heavy chain includes one variable region and three constant domains, whereas each light chain includes one variable region and one constant domain. The variable region of each of the heavy chain and the light chain includes three complementarity-determining regions (referred to as "CDRs") and four framework regions. CDRs function to bind to epitopes of antibodies. CDRs on each chain start from the N-terminus and are aligned in the order CDR1, CDR2, and CDR3. These CDRs are distinguished from one another by the chain on which they are positioned.

The antibody according to the present invention, for example, includes a heavy chain variable region including CDR1 of SEQ ID NO: 1, CDR2 of SEQ ID NO: 2 and CDR3 of Tyr His Phe, and a light chain variable region including CDR1 of SEQ ID NO: 3, CDR2 of SEQ ID NO: 4, and CDR3 of SEQ ID NO: 5.

In addition, the antibody according to the present invention may include: a heavy chain variable region framework region (FR) selected from the group consisting of SEQ ID NOS: 6 to 9; and a light chain variable region framework region (FR) selected from the group consisting of SEQ ID NOS: 10 to 13.

In addition, the antibody according to the present invention may include a heavy chain variable region of SEQ ID NO: 14 and a light chain variable region of SEQ ID NO: 15, and may include a heavy chain of SEQ ID NO: 16 and a light chain of SEQ ID NO: 17.

The antibody according to the present invention includes polyclonal antibodies, monoclonal antibodies, whole antibodies and antibody fragments. In addition, chimeric antibodies (e.g., humanized mouse antibodies), bivalent or bispecific molecules (e.g., bispecific antibodies), diabodies, triabodies and tetrabodies fall within the scope of the antibody used in the present invention.

The term "monoclonal antibody" as used herein refers to an antibody molecule having a uniform molecule composition which is obtained from a substantially identical population of antibodies and exhibits binding specificity and affinity to a single epitope.

A "humanized"-type non-human (e.g., murine) antibody is a chimeric antibody that contains a minimal sequence derived from non-human immunoglobulin. In most cases, the humanized antibody is a human immunoglobulin (acceptor antibody) in which a residue from the hypervariable region of an acceptor is replaced by a residue from the hypervariable region of a non-human species (donor antibody) having the desired specificity, affinity and ability, such as a mouse, rat, rabbit or non-human primate.

The term "human antibody" as used herein refers to a molecule that consists entirely of amino acid sequences of all components of human immunoglobulin including CDRs, framework regions and the like. Human antibodies have at least three potential benefits in the treatment of human diseases. First, human antibodies further preferably interact with the human immune system to mediate more effectively the destruction of target cells by, for example, complement-dependent cytotoxicity (CDC) or antibody-dependent cell-mediated cytotoxicity (ADCC). Another benefit is that the human immune system does not recognize the human antibody as being an exogenic molecule so that adverse effects caused by formation of immune complexes that may occur in chimeric antibodies or humanized antibodies can be minimized when administered to the human body. Third, such formation of immune complexes may lead to shortened half-lives of chimeric or humanized antibody preparations administered to the human body, but the half-lives of human antibodies are similar to those of antibodies naturally derived from the human circulatory system, even when administered in smaller amounts or at a lower frequency.

When the antibody according to the present invention includes a constant domain, it may be derived from IgG, IgA, IgD, IgE, IgM, or a combination or hybrid thereof.

The term "combination" as used herein means that a polypeptide encoding a single-chain immunoglobulin Fc fragment having the identical origin is linked to a single-chain polypeptide having a different origin in order to produce a dimer or multimer. Such a dimer or multimer may be produced from two or more constant domains selected from the group consisting of the constant domains of IgG, IgA, IgD, IgE and IgM.

The term "hybrid" as used herein means that sequences encoding two or more heavy chain constant domains having different origins are present in a single-chain immunoglobulin heavy chain constant domain. For example, a domain hybrid may be composed of one to four domains selected from the group consisting of CH1, CH2, CH3 and CH4 of IgG, IgA, IgD, IgE and IgM. In addition, a combination of hybrids may be formed from heavy chain constant domains of IgG subtypes, i.e., IgG1, IgG2, IgG3 and IgG4. The combination of hybrids is as defined above.

The antibody or antibody fragment of the present invention may include the sequence of the anti-coagulation factor VIII antibody mentioned herein as well as biological equivalents thereof, as long as it meets the criterion of specifically recognizing the coagulation factor VIII. For example, additional changes can be made to the amino acid sequence of the antibody in order to further improve the binding affinity and/or other biological properties of the antibody. Such modifications include, for example, deletion, insertion and/or substitution of the amino acid sequence residues of the antibody. Such amino acid variations are based on the relative similarity of amino acid side chain substituents, such as the hydropathicity, hydrophilicity, charge and size thereof. It can be seen through analysis of the size, shape and type of amino acid side chain substituents that all of arginine, lysine and histidine are classified as basic positively-charged residues; alanine, glycine and serine are classified as amino acids which are similar and small in size; and phenylalanine, tryptophan and tyrosine are classified as amino acids having aromatic side chains. Thus, based on these considerations, arginine, lysine and histidine; alanine, glycine and serine; and phenylalanine, tryptophan and tyrosine are considered to be biologically functional equivalents.

The hydropathic index of amino acids may be considered in introducing mutations. Each amino acid is given a hydropathic index depending on a hydropathicity and charge thereof: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydropathic index of amino acids is very important in imparting the interactive biological function of proteins. It is well-known that substitution with an amino acid having a similar hydropathic index is needed in order to retain similar biological activity. When a mutation is introduced with reference to a hydropathic index, substitution is made between amino acids having a hydropathic index difference preferably within ±2, more preferably within ±1, and even more preferably within ±0.5.

Meanwhile, it is also well-known that substitution between amino acids having similar hydrophilicity values leads to proteins having equivalent biological activity. As disclosed in U.S. Pat. No. 4,554,101, the following hydrophilicity values are given to respective amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

Amino acid exchange in proteins that does not entirely change the activity of the molecule is known in the art (H. Neurath and R. L. Hill (Eds), "The Proteins", Academic Press, New York, 1979). The most common exchange is exchange between the amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu and Asp/Gly.

When taking into consideration variations having biologically equivalent activity, the antibody or a nucleotide molecule encoding the same according to the present invention is interpreted to include a sequence having substantial identity with the sequence set forth in the sequence number. The term "substantial identity" means that a sequence has a homology of at least 61%, more preferably a homology of 70%, even more preferably a homology of 80%, and most preferably a homology of 90%, when aligning the sequence of the present invention with any other sequence so as to correspond to each other as much as possible and analyzing the aligned sequence using algorithms commonly used in the art. The NCBI Basic Local Alignment Search Tool (BLAST) is accessible from NCBI or the like and can be used in conjunction with sequence analysis programs such as BLASTP, BLASM, BLASTX, TBLASTN and TBLASTX over the Internet. BLAST is available at www.ncbi.nlm.nih.gov/BLAST/. A method of comparing a sequence homology using this program can be found at www.ncbi.nlm.nih.gov/BLAST/blast_help.html.

In another aspect, the present invention is directed to a polynucleotide encoding the antibody or an antigen-binding fragment thereof.

By isolating the polynucleotide encoding the antibody or an antigen-binding fragment thereof according to the present invention, an antibody or antigen-binding fragment thereof can be produced recombinantly. The polynucleotide is isolated and inserted into a replicable vector for further cloning (amplification of DNA) or further expression. Based on this, in another aspect, the present invention is directed to a vector including the polynucleotide.

The term "nucleotide" is intended to encompass both DNA (gDNA and cDNA) and RNA molecules, and a nucleotide, of which is a basic constituent unit, includes naturally derived nucleotides as well as analogues wherein sugar or base moieties are modified. The sequence of the polynucleotide encoding heavy and light chain variable regions of the present invention can be varied. Such variation includes addition, deletion, or non-conservative or conservative substitution of nucleotides.

In one embodiment, the present invention may be a polynucleotide encoding the heavy chain variable region of SEQ ID NO: 19 or a polynucleotide encoding the light chain variable region of SEQ ID NO: 20. In another embodiment, the present invention may be a polynucleotide encoding the heavy chain of SEQ ID NO: 21 or a polynucleotide encoding the light chain of SEQ ID NO: 22.

The present invention is interpreted to include a nucleotide sequence having substantial identity with the nucleotide sequence. The nucleotide sequence having substantial identity means a nucleotide sequence that has a homology of at least 80%, more preferably a homology of at least 90%, and most preferably a homology of at least 95%, when aligning the sequence of the present invention with any other sequence so as to correspond to each other as much as possible and analyzing the aligned sequence using algorithms commonly used in the art.

The DNA encoding the antibody can be easily separated or synthesized using conventional procedures (for example, using an oligonucleotide probe capable of specifically binding to DNA encoding heavy and light chains of the antibody). A variety of vectors are obtainable. Vector components generally include, but are not limited to, one or more of the following components: 1) signal sequences (signal peptides), 2) replication origins, 3) one or more marker genes, 4) enhancer elements, and 5) promoters and transcription termination sequences.

As used herein, the term "vector" refers to a means for expressing target genes in host cells and includes plasmid vectors and cosmid vectors, as well as viral vectors such as bacteriophage vectors, adenovirus vectors, retroviral vectors and adeno-associated viral vectors (AAV). The polynucleotide encoding the antibody in the vector is operably linked to a promoter.

The term "operably linked" means a functional linkage between a polynucleotide expression regulation sequence (e.g., promoter, signal sequence or array of transcription regulator binding site) and another polynucleotide sequence, and is regulated by transcription and/or translation of the polynucleotide sequence.

When a prokaryotic cell is used as a host, the vector generally includes a potent promoter capable of conducting transcription (such as tac promoter, lac promoter, lacUV5 promoter, ipp promoter, pLX promoter, pRX promoter, rac5 promoter, amp promoter, recA promoter, SP6 promoter, trp promoter, or T7 promoter), a ribosome binding site for initiation of translation, and a transcription/translation termination sequence. In addition, for example, when a eukaryotic cell is used as a host, the vector includes a promoter (e.g., a metallothionein promoter, a R-actin promoter, a human hemoglobin promoter and a human muscle creatine promoter) derived from the genome of mammalian cells, or a promoter derived from an animal virus such as adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein Barr virus (EBV) promoter, and Rous sarcoma virus (RSV) promoter, and generally has a polyadenylation sequence as a transcription termination sequence.

Optionally, the vector may be fused with another sequence in order to facilitate purification of the antibody expressed therefrom. The sequence to be fused includes, for example, glutathione S-transferase (Pharmacia, USA), maltose-binding protein (NEB, USA), FLAG (IBI, USA), 6× His (hexahistidine; Qiagen, USA) and the like.

The vector includes antibiotic-resistant genes commonly used in the art as selectable markers, and examples thereof include genes resistant to ampicillin, gentamycin, carbenicillin, chloramphenicol, streptomycin, kanamycin, geneticin, neomycin and tetracycline.

In another aspect, the present invention is directed to a cell transformed with the above-mentioned vector. The cell used to produce the antibody of the present invention may be a prokaryote, yeast or higher eukaryotic cell, but is not limited thereto.

Prokaryotic host cells such as *Escherichia coli*, the genus *Bacillus* such as, *Bacillus subtilis* and *Bacillus thuringiensis*, *Streptomyces* spp., *Pseudomonas* spp. (for example, *Pseudomonas putida*), *Proteus mirabilis* and *Staphylococcus* spp. (for example, *Staphylococcus carnosus*) can be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

In another aspect, the present invention is directed to a method for producing the antibody or an antigen-binding fragment thereof, including: culturing the recombinant host cells to produce an antibody or an antigen-binding fragment thereof and recovering the antibody or an antigen-binding fragment thereof, followed by isolation and purification.

The cells can be cultured in various media. Any commercially available medium can be used as a culture medium without limitation. All other essential supplements well-known to those skilled in the art may be included in appropriate concentrations. Culture conditions such as temperature and pH are conventionally used with host cells selected for expression, which will be apparent to those skilled in the art.

The recovery of the antibody or antigen-binding fragment thereof can be carried out, for example, by centrifugation or ultrafiltration to remove impurities and purification of the resulting product using, for example, affinity chromatography. Other additional purification techniques such as anion or cation exchange chromatography, hydrophobic interaction chromatography and hydroxyapatite (HA) chromatography may be used.

In another aspect, the present invention is directed to a column for isolating or purifying a recombinant coagulation factor VIII, to which the antibody or an antigen-binding fragment thereof binds.

"Isolation and purification" refers to a series of methods/processes for distinguishing a certain protein, e.g., coagulation factor VIII, from impurities present in a complex mixture and removing other impurities in order to enhance purity or quality. Depending on the anti-coagulation factor VIII antibody that is attached to the column, the coagulation factor VIII specifically binding to the antibody is detected from the impurities present in the sample. The impurities may for example include host cell proteins, host cell residues, cell lysates and proteins, DNA, endotoxins, and culture factors for cell growth.

The term "column" as used herein refers to a device filled with a stationary phase used for a chromatographic procedure for the separation, detection or purification of a target protein (such as recombinant coagulation factor VIII) from a complex mixture using the physical-chemical properties of the target protein. Specifically, the target protein can be selectively separated from a mixture or an impurity by producing a column filled with the stationary phase depending on the degree of hydrophilicity or hydrophobicity of the target material, the potential of the molecule, the possibility of binding to a specific substance, and the like.

The column may be filled with a stationary phase material having affinity for coagulation factor VIII, and the stationary phase material may be, for example, a resin or an agarose bead. As described in one embodiment of the present invention, produced is a column for separation or purification of a recombinant coagulation factor VIII, which is filled with a stationary phase in which an anti-coagulation factor VIII antibody, serving as a ligand, is linked to Sepharose, which is a resin in the form of a cross-linked agarose bead.

In another aspect, the present invention is directed to a method of purifying a coagulation factor VIII including allowing a sample containing a recombinant coagulation factor VIII to interact with a ligand linked to the stationary phase of the column.

The sample to be loaded into the column may be, for example, a cell culture liquid or a fermentation broth, and when the sample is loaded into the column and the purification process is performed, host cell proteins and host cell residues other than the target protein, for example, cell lysates and proteins, DNA and endotoxins, can be removed.

The recombinant coagulation factor VIII contained in the sample binds to the anti-coagulation factor VIII antibody linked to the column stationary phase through an antigen-antibody reaction. Then, the recombinant coagulation factor VIII binding to the anti-coagulation factor VIII antibody can be isolated through a separate elution procedure. The composition and elution conditions of the eluate can be set to conditions that can be implemented by those skilled in the art and can be combined with a suitable buffer or liquid to provide a mobile phase.

This allows substantially pure recombinant coagulation factor VIII to be isolated and purified. "Substantially pure" means that substantially all of the material other than the recombinant coagulation factor VIII is removed, and advantageously about 80% or more, for example, about 95% or more, i.e., 95 to 100%, for example, about 98% or more, i.e., 98 to 100%, preferably about 99% or more, i.e., 99 to 100%, based on the total amount of a contaminant, may be removed. The degree of purity that is possible may be determined based on the concentration of the recombinant coagulation factor VIII in the sample applied to the column and other conditions used.

Hereinafter, the present invention will be described in more detail with reference to examples. However, it will be obvious to those skilled in the art that these examples are provided only for illustration of the present invention and should not be construed as limiting the scope of the present invention.

Example 1: Production of Hybridoma

The recombinant coagulation factor VIII protein to be used for vaccination (immunization) was prepared through isolation from a cell culture solution and purification in order to produce a monoclonal antibody of the recombinant coagulation factor VIII protein (SEQ ID NO: 18). Balb/c mice were used for immunization.

The recombinant coagulation factor VIII protein and an antigen adjuvant (Freund's complete adjuvant) were thoroughly mixed in equivalent amounts, and the resulting mixture was intraperitoneally injected into the Balb/c mice. 25 days later, the recombinant coagulation factor VIII protein and the antigen adjuvant were mixed in equivalent amounts, the resulting mixture was further injected into the mice, the serum was collected from the mice, and additional injection was conducted until the recombinant coagulation factor VIII protein showed an excellent positive reaction.

On the third day after the last vaccination (immunization), the serum was collected from the mice and whether or not antibodies were produced in the serum was identified through enzyme-linked immunosorbent assay (ELISA). Then, the abdomen of each mouse was opened and the spleen was taken out and pulverized. The pulverized splenocytes were fused with mouse myeloma cells (SP2/0) according to a known method (Galfre G. et al., Nature 266, 550-552 (1977)). Mouse splenocytes and mouse myeloma cells equivalent to ⅕ of the splenocytes were prepared and mixed with PEG1500, followed by inducing a fusion reaction. After the fusion reaction, the cells were suspended in a selective medium containing HAT (hypoxanthine, aminopterin, thymidine) and transferred to a 96-well plate to inhibit the growth of unfused cells. When the fused cells were sufficiently grown while the medium was replaced with a selective medium containing HAT, analysis was conducted through ELISA specific for coagulation factor VIII protein, and cells showing a positive reaction were transferred to a new plate and then cultured therein. When the count of cells was sufficient, single clonal production cell line selection was conducted through limiting dilution. 33 clones showing positive responses were selected through ELISA using the culture solution of the well where colonies were formed. After identifying the binding ability of the culture solution of selected clones to the antigen using Biacore, two clones (3F6-2-5 and 5F4-9-1), which were considered to be the most suitable for use as antibodies for purifying the recombinant coagulation factor VIII protein, were selected. 3F6-2-5, which has better binding ability to the antigen among the two clones, was selected as an antibody-producing hybridoma clone for the recombinant coagulation factor VIII protein. The results of analysis of the isotype of the antibody produced by the 3F6-2-5 clone showed that the heavy chain was IgG1 and the light chain was an antibody belonging to the kappa group.

Example 2: Antibody Gene Securing

The heavy and light chain genes of an antibody against a recombinant coagulation factor VIII protein (FVIII) (hereinafter referred to as anti-FVIII antibody) were obtained by extracting RNA from mouse hybridoma cells (3F6-2-5) producing antibodies against FVIII, followed by RT-PCR.

In order to secure heavy chain genes, RNA was extracted from 3F6-2-5 hybridoma cells and subjected to 5' RACE. GSP1 (gene-specific primer), GSP2 and a nested primer for the 3' constant region were prepared, RACE PCR was performed, the resulting PCR product was cloned into the T-vector, and then the nucleotide sequence was analyzed. As a result, the nucleotide sequence of the 5' region including a signal sequence was identified. Primers were produced according to the identified nucleotide sequences and heavy chain genes were obtained through RT-PCR.

```
                              (SEQ ID NO: 23)
GSP1:       5'-TGAGGAGACGGTGACCGTGGT (SEQ ID NO: 24)
GSP2:       5'-CCTTGGCCCCAGAAGTGGTAA
```

```
                              (SEQ ID NO: 25)
Nested:     5'-TAAATGCCAGTGICTICAGC
```

After identifying the nucleotide sequences, primers were constructed so as to include the 5'-Nhe I and 3'-Xho I restriction enzyme recognition sequences in order to clone heavy chain genes into the Pangen expression vector (pPGIX), and then the heavy chain genes inserted into the T-vector were amplified. The PCR products and expression vectors were treated with Nhe I and Xho I restriction enzymes, pPGIX-anti-FVIII-HC was produced, and the nucleotide sequence of the inserted heavy chain gene was identified (SEQ ID NO: 21).

The light chain genes were obtained by extracting RNA from 3F6-2-5 hybridoma cells and conducting RT-PCR using 11 types of 5'-primers and primer (MKCIII) for 3'-constant regions produced based on the known signal sequence.

The results of RT-PCR identified a 700 bp band including the light chain variable region and the constant region in the PCR product using the MKV7 primer and the 3'-MKCIII primer. The obtained PCR products were cloned into the T-vector, and the nucleotide sequences were then identified.

```
MKV1:
                                      (SEQ ID NO: 26)
5'-GCT AGC GCC ACC ATG AAG TTG CCT GTT AGG CTG TTG
GTG CTG

MKV2:
                                      (SEQ ID NO: 27)
5'-GCT AGC GCC ACC ATG GAG WCA GAC ACA CTC CTG YTA
TGG GTG

MKV3:
                                      (SEQ ID NO: 28)
5'-GCT AGC GCC ACC ATG AGT GTG CTC ACT CAG GTC CTG
GSG TTG

MKV4:
                                      (SEQ ID NO: 29)
5'-GCT AGC GCC ACC ATG AGG RCC CCT GCT CAG WTT YTT
GGM WTC

MKV5:
                                      (SEQ ID NO: 30)
5'-GCT AGC GCC ACC ATG GAT TTW CAG GTG CAG ATT WTC
AGC TTC

MKV6:
                                      (SEQ ID NO: 31)
5'-GCT AGC GCC ACC ATG AGG TKC YYT GYT SAG YTY CTG
RGG

MKV7:
                                      (SEQ ID NO: 32)
5'-GCT AGC GCC ACC ATG GGC WTC AAG ATG GAG TCA CAK
WYY CWG G

MKV8:
                                      (SEQ ID NO: 33)
5'-GCT AGC GCC ACC ATG TGG GGA YCT KTT TYC MMT TTT
TCA ATT G
```

-continued

MKV9:
(SEQ ID NO: 34)
5'-GCT AGC GCC ACC ATG GTR TCC WCA SCT CAG TTC CTT G

MKV10:
(SEQ ID NO: 35)
5'-GCT AGC GCC ACC ATG TAT ATA TGT TTG TTG TCT ATT TCT

MKV11:
(SEQ ID NO: 36)
5'-GCT AGC GCC ACC ATG GAA GCC CCA GCT CAG CTT CTC TTC C

MKCIII:
(SEQ ID NO: 37)
5'-CTA ACA CTC ATT CCT GTT GAA GCT C

After identifying the nucleotide sequences, primers were prepared so as to include the 5'-Nhe I and 3'-Xho I restriction enzyme recognition sequences in order to clone the light chain genes into the Pangen's expression vector (pPGIX), and the light chain genes inserted into the T-vector were then amplified using PCR. The PCR products and expression vectors were treated with Nhe I and Xho I restriction enzymes and then ligated to produce pPGIX-anti-FVIII-LC, and then the nucleotide sequence of the inserted light chain gene was identified (SEQ ID NO: 22). The heavy and light chain genes inserted into the expression plasmids, pPGIX-Anti-FVIII-HC and pPGIX-anti-FVIII-LC, were transferred to the Pangen's expression vector (pPGX) and used for transfection in order to develop a cell line having higher expression efficiency. The pPGX-anti-FVIII-HC and pPGX-Anti-FVIII-LC plasmid DNA was treated with Nhe I and Xho I restriction enzymes and then ligated to pPGX treated with the same restriction enzymes, to construct pPGX-Anti-FVIII-HC and pPGX-Anti-FVIII-LC plasmid DNA, respectively.

Example 3: CHO Cell Expression

The transfection of the expression plasmids with the CHO DG44 host cell line was carried out in 24 wells, and pPGX-anti-FVIII-HC, pPGX-anti-FVIII-LC and pDCH1P (dhfr) were simultaneously transfected by electroporation. When the cells were fully grown after being cultured in a 37° C., 5% CO2 incubator, the cells were cultured in a selective medium so as to grow only the transformed cells. Approximately two weeks later, when the cells were sufficiently grown, a portion of the culture supernatant was taken and the anti-FVIII-antibody-expressing cell group was selected through ELISA analysis. In order to select stable cell lines with high expression efficiency, single cell selection was performed by selecting five cell lines (ADBA1001, ADBA1003, ADBA1011, ADBA1013, ADBA1014), based on the results of the ELISA analysis. Cells were seeded in a 96-well plate at a density of 1 cell/well in the culture medium, and colonies formed after about 4 weeks were analyzed to select cell lines having high expression efficiency, and the cell lines were cultured. When a sufficient number of cells were obtained, the expression efficiency of monoclonal cell lines was comparatively analyzed through ELISA. Six monoclonal cell lines having high production efficiency (ADBA1003-22, ADBA1011-19, ADBA1013-14, ADBA1013-27, ADBA1014-11, ADBA1014-69) were selected as candidate cell lines.

Six monoclonal cell lines having high antibody productivity were identified to stably express antibody proteins during 90 days of long-term subculture. Among them, the ADBA1013-14 cell line having the highest antibody productivity was selected as the final cell line. It was identified that the antibody produced therefrom had the sequence shown in Table 1.

TABLE 1

|  | CDR1 | CDR2 | CDR3 |
|---|---|---|---|
| Heavy region CDR | GFTFSDAWMD (SEQ ID NO: 1) | EIRSKAKNHATNY AESVKG (SEQ ID NO: 2) | YHF |
| Heavy region variable region | EVKIEESGGGLVQPGGSMKLSCAASGFTFSDAWMDWVRQSPEK GLEWVAEIRSKAKNHATNY AESVKGRFT ISRDDSKSRVYLQMNTLRAE DTGIYYCTNYHFWGPGTTLT VS (SEQ ID NO: 14) | | |
| Light chain CDR | KSSQSLLNSINQEN YLA (SEQ ID NO: 3) | FGSTRES (SEQ ID NO: 4) | QQHYSTPYT (SEQ ID NO: 5) |
| Light chain variable region | DIVMTQ SPSSLAMSVG QKVTMSCKSS QSLLNSINQENYLAWYQQKP GQSPKLLIY FGSTRESGVPD RFIGSGSGTD FSLTISDVQA EDLADYFCQQHYSTPYTFGG GTKLEMKRA (SEQ ID NO: 15) | | |

Example 4: Antibody Purification

Antibody proteins were isolated and purified using the culture solution of the ADABA1013-14 cell line. Affinity chromatography was performed using a column filled with a protein A resin. Columns were mounted in an AKTA Pure system (GE healthcare) and were equilibrated with an equilibrium buffer of 20 mM sodium phosphate and 150 mM sodium chloride (pH 7.4), and the culture solution was loaded thereon. Then, the column was washed and only an antibody protein was eluted with 20 mM sodium citrate (pH 3.5) as an elution buffer. For the virus inactivation of the eluted protein fraction, the pH of the eluate was lowered to 3.5 with 1N HCl and the eluate was reacted at room temperature for 180 minutes.

After virus inactivation, the eluate were diluted with four times the volume of water for injection and subjected to Q Sepharose column chromatography. Columns were mounted in an AKTA Pure system (GE healthcare), were equilibrated with an equilibrium buffer of 4 mM citric acid and 10 mM sodium phosphate, and the samples were loaded thereon. The flowthrough (effluent) was collected during sample loading, filtered through a 0.22 μm PES membrane, and subjected to nanofiltration.

Example 5: Characterization of Purified Antibodies

1. N-Glycosylation Site Determination

The N-glycosylation site of the purified antibody protein was identified using peptide-mapping analysis.

The purified antibody protein was desalted and concentrated using a trichloroacetic acid precipitation method. The obtained sample was reduced and alkylated through treatment with Trypsin and Trypsin/PNGase F, followed by treatment with DTT and iodoacetamide. The results of analysis of glycosylated asparagine amino acid positions through LC-MS/MS peptide sequencing analysis using the sample before and after treatment with PNGase F showed that the sugar was bonded to Asparagine No. 288 of the heavy chain.

2. Identification (Isoelectric Focusing) of Isoelectric Point (pI)

The purified antibody protein was separated according to the isoelectric point (pI) to determine the isoelectric point of the antibody.

20 μg of an IEF marker (pI 3-10) and the purified antibody protein were loaded onto a Novex® pH 3-7 IEF gel and electrophoresis was performed for 1 hour, 1 hour, and 30 minutes at voltages of 100V, 200V, and 500V, respectively. The gel was fixed in 12% TCA (trichloroacetic acid) for 30 minutes, washed three times with ultrapure water for 10 minutes, and treated until staining with GelCode Blue Stain Reagent was sufficient. After the staining was completed, the antibody was washed with ultrapure water, a pI band was identified with the naked eye, and the pI value was analyzed using a Gel Doc XR+imager.

The pI of the IEF band was analyzed using a Gel Doc XR+imager. As a result, the pI of the purified antibody protein was found to be 6.2 to 6.8 (FIG. 1).

3. Intact Molecular Weight Determination

The one-dimensional structure of the protein was identified by measuring the molecular weight of the purified antibody protein.

The purified antibody protein diluted to 1 mg/mL was treated with a 1M DTT solution at a final concentration of 20 mM and reacted at room temperature for 40 minutes, and the molecular weight of the heavy chain/light chain was measured using LC-MS.

The peptides isolated during HPLC were connected to the ESI source of the Q-TOF MS to determine the mass value of the peptide ions. The molecular weight was determined using DataAnalysis software and analyzed by deconvolution using a maximum entropy method.

The molecular weight of the native form of the purified antibody protein was found to be 147,859 to 148,394 Da. This was about 3,000 Da higher than the molecular weight of the theoretical antibody protein, excluding the molecular weight of sugar, which was considered to be the average of the molecular weights of sugars bonded to two heavy chains. The molecular weight of the light chain was measured to be 24,323 Da (±2 Da), which was exactly the same as the light chain molecular weight of the theoretical antibody protein. The major molecular weight of the heavy chain was detected to be 49,715 Da. This was increased by about 1,300 Da compared to the molecular weight of the theoretical heavy chain, which is considered to be due to the molecular weight of the sugar bonded to the Asn 288 of the heavy chain.

4. Western Blotting

The immunological characteristics of the purified antibody protein through antigen-antibody reaction were analyzed.

The purified antibody protein was diluted to 1 mg/mL, 1, 3, and 5 μg of the dilution were prepared, and PBS was added thereto at a final volume of 10 μL. After mixing 2.5 μL of a 5× non-reducing sample buffer with 2.5 μL of a 5× reducing sample buffer, the sample was prepared under reducing conditions by boiling at 95° C. or higher for 10 minutes and cooling on the ice for 5 minutes. The prepared sample was loaded on a 10% SDS-PAGE gel and then subjected to electrophoresis at 80V for 30 minutes and at 100V for 1 hour 30 minutes. After running, the cells were transferred to a nitrocellulose membrane and blocked with 5% skim milk for 1 hour. After blocking, the goat anti-mouse IgG, AP conjugate diluted to 1:1,000 was treated at room temperature for 2 hours and then washed with 1×TBST for 10 minutes three times. After washing, the membrane was treated with NBT/BCIP for protein detection to induce color development. After observing sufficient color development, the reaction was stopped by washing with running water.

Figure 2:
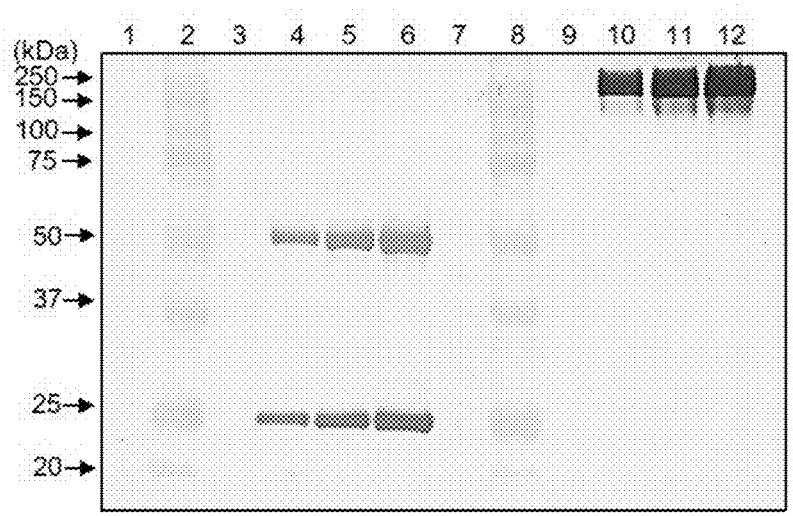
FIG. 2 shows the results of identifying the immunological characteristics of the purified antibody protein through western blotting.

As a result of western blotting, under reducing conditions, the light chain was detected at about 25 kDa and the heavy chain was detected at about 50 kDa, and under the non-reducing conditions, the antibody protein was detected at about 150 kDa (FIG. 2). Thus, it was identified that the purified antibody protein, mouse IgG, specifically binds to anti-mouse IgG antibody.

5. Identification of Specific Binding to FVIII

Whether or not the purified anti-FVIII antibody protein specifically binds to the antigen, recombinant coagulation factor FVIII was identified through antigen-antibody reaction.

200 and 400 ng of the recombinant coagulation factor FVIII diluted to 0.02 mg/mL were prepared and PBS was added thereto to achieve a final volume of 20 μL. The resulting mixture was mixed with 5 μL of a 5× reducing sample buffer, boiled at a temperature of 95° C. or higher for 10 minutes and cooled on ice for 5 minutes to prepare a sample. The prepared sample was loaded on a 7.5% gel and then subjected to electrophoresis at 80V for 30 minutes and at 100V for 1 hour 30 minutes. After running, the cells were transferred to a nitrocellulose membrane and blocked with 5% skim milk for 1 hour. After blocking, the purified antibody protein (mouse IgG), diluted to 1:1,000, was treated at 4° C. overnight and then washed with 1×TBST for 10 minutes three times. After washing, the secondary antibody (goat anti-mouse IgG, AP conjugate) diluted to 1:5,000 was reacted at room temperature for 2 hours and then washed three times for 10 minutes with 1×TBST. The membrane was treated with NBT/BCIP to induce color development for protein detection. After observing sufficient color development, the reaction was stopped by washing with running water.

Figure 3:
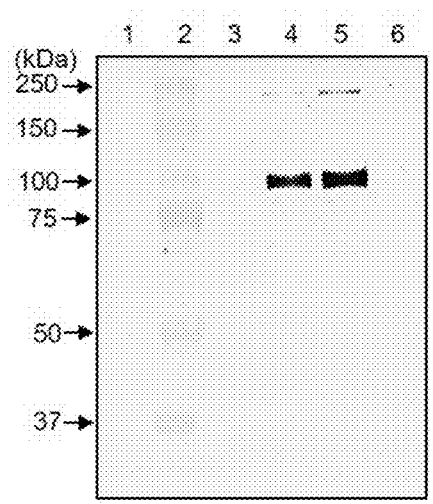
FIG. 3 shows the result of identifying whether or not the purified anti-FVIII antibody protein specifically binds to an antigenic recombinant coagulation factor FVIII through antigen-antibody reaction.

As a result of western blotting, as shown in the drawing, bands were detected in the vicinity of 90 kDa corresponding to the heavy chain of the coagulation factor FVIII, which means that the purified antibody protein specifically binds to the coagulation factor FVIII (FIG. 3).

6. Antibody Binding Affinity (SPR)

The kinetic affinity (Ka, Kd, KD) between the purified antibody protein and the recombinant coagulation factor FVIII protein through antigen-antibody reaction was measured by a SPR (surface plasmon resonance) method.

The CM5 chip was mounted on a Biacore T200 instrument, and the recombinant coagulation factor FVIII protein as a ligand was diluted in a 10 mM sodium acetate buffer (pH 5.0) and injected into a sample channel for 10 minutes for immobilization. The purified antibody protein, as the analyte, was prepared at a concentration of 2 μM by diluting with a buffer and was then serially diluted to ten concentrations (0.0039, 0.0078, 0.015, 0.031, 0.062, 0.125, 0.25, 0.5, 1, 2 μM). Association and dissociation times were set to 3 minutes and 4 minutes, respectively, and association and dissociation were measured.

BIAevaluation analysis software was used to analyze the kinetic affinity of the purified antibody protein and the recombinant coagulation factor FVIII protein. The association force, dissociation force and dissociation constant were calculated as follows by applying ten concentrations of association/dissociation data to a 1:1 kinetic binding model (A+B↔AB).

As a result of the SPR test, the KD value of the purified antibody protein for the recombinant coagulation factor FVIII protein was analyzed and determined to be $5.53E^{-08}$ M.

TABLE 2

| Name | $K_a$ (M$^{-1}$s$^{-1}$) | $K_d$ (s$^{-1}$) | $K_D$ (M) | $R_{max}$ (μRIU) |
|---|---|---|---|---|
| Anti-FVIII antibody | $1.23E^{+04}$ | $6.80E^{-04}$ | $5.53E^{-08}$ | 701.2 |

Example 6: Production of Column for Antigen Purification

The Mab gel was prepared using the purified antibody to produce a column for purifying a recombinant coagulation factor FVIII protein as a hemophilia medicine.

The purified antibody was exchanged with a coupling buffer solution (sodium bicarbonate, sodium phosphate, pH 8.3) for coupling to a CNBr-activated Sepharose 4B resin.

The CNBr-activated Sepharose 4B resin was converted into a slurry by swelling with 1N HCl, mixed with the antibody exchanged with the coupling buffer, and reacted at room temperature for 2 hours. After alternately washing the resin with a washing solution with a low pH and a washing solution with a high pH, preparation of the Mab gel was completed.

Example 7: Identification of Antigen-Antibody Binding

In order to identify the binding ability of the prepared Mab gel to the recombinant coagulation factor FVIII protein, a performance test was conducted using a culture solution of the recombinant coagulation factor FVIII protein. After the Mab gel-filled column was equilibrated with an equilibration buffer, a culture solution containing 5000 IU of the recombinant FVIII protein was loaded. Nonspecifically binding proteins were removed with a washing buffer and then proteins were eluted.

The recombinant FVIII culture solution, eluate and flow-through were quantitatively analyzed by chromogenic assay. As a result of the analysis, it was confirmed that approximately 85% of the recombinant FVIII protein was bound to the Mab gel and was then eluted.

Therefore, the Mab gel for purification produced using the produced antibody was found to be capable of binding to the recombinant coagulation factor FVIII protein and thus to be suitably used for the production of an antibody resin for purification in order to commercially produce the recombinant coagulation factor FVIII protein.

Example 8 Purification of Recombinant Coagulation Factor FVIII Using Mab Gel for Purification Immunoaffinity chromatography was conducted using a 50 L culture solution in order to identify whether or not the produced Mab gel for purification was suitable as a resin for purification in order to commercially produce the recombinant coagulation factor FVIII.

A column (diameter: 11.6 cm, height: 9.5 cm) filled with a Mab gel (about 1,000 mL) for purification was used for purification. The column was mounted in an AKTA Pure system (GE healthcare) and equilibrated. When the column was stabilized, only half of the culture solution was loaded, washed for 3 CV, and eluted for 7 to 9 CV. The remaining culture medium was loaded on the column in the same manner, immunoaffinity chromatography was performed, and the eluted recombinant coagulation factor FVIII was recovered. The recovered recombinant coagulation factor FVIII was filtered through a 0.22 μm PES membrane and then stored at 4° C.

A chromogenic assay was performed using pre- and post-purification samples in order to determine the purification yield of the immunoaffinity chromatography. The results of activity analysis showed that the recombinant coagulation factor FVIII contained in 50 L of the culture solution was 3.95 MIU and the purified protein was 3.25 MIU, and thus the purification yield was found to be 82.3%.

Therefore, it was considered that the Mab gel for purification produced using the produced antibody is capable of binding to the recombinant coagulation factor FVIII protein on a commercial production scale, and thus is suitable for use as an antibody resin for purification in order to commercially produce the recombinant coagulation factor FVIII protein.

INDUSTRIAL APPLICABILITY

Since the antibody or antigen-binding fragment thereof that specifically binds to a coagulation factor FVIII according to the present invention exhibits excellent affinity and binding ability to a coagulation factor FVIII, purification of high-purity recombinant coagulation factor FVIII and production of stable coagulation factor FVIII with improved quality are possible by providing a column for isolating or purifying a recombinant coagulation factor FVIII, to which the antibody or antigen-binding fragment thereof is coupled, or a method of purifying the recombinant coagulation factor FVIII using the column.

Although the present invention has been described in detail with reference to specific configurations, those skilled in the art will appreciate that this description is provided as preferred embodiments for illustrative purposes and should not be construed as limiting the scope of the present invention. Therefore, the substantial scope of the present invention is defined by the accompanying claims filed and equivalents thereto.

SEQUENCE LISTING FREE TEXT

An electronic file is attached.

The invention claimed is:

1. An antibody binding specifically to a coagulation factor VIII, or an antibody-binding fragment thereof, comprising:
   a heavy chain variable region including CDR1 of SEQ ID NO: 1, CDR2 of SEQ ID NO: 2, and CDR3 of Tyr His Phe; and
   a light chain variable region including CDR1 of SEQ ID NO: 3, CDR2 of SEQ ID NO: 4, and CDR3 of SEQ ID NO: 5.

2. The antibody or antibody-binding fragment thereof according to claim 1, wherein the antibody or antibody-binding fragment comprises:
   a heavy chain variable region framework region (FR) selected from the group consisting of SEQ ID NOS: 6 to 9; and
   a light chain variable region framework region (FR) selected from the group consisting of SEQ ID NOS: 10 to 13.

3. The antibody or antibody-binding fragment thereof according to claim 1, wherein the antibody or antibody-binding fragment thereof comprises a heavy chain variable region of SEQ ID NO: 14 and a light chain variable region of SEQ ID NO: 15.

4. The antibody or antibody-binding fragment thereof according to claim 1, wherein the antibody or antibody-binding fragment thereof comprises a heavy chain of SEQ ID NO: 16 and a light chain of SEQ ID NO: 17.

5. A polynucleotide encoding the antibody or antigen-binding fragment thereof according to any one of claims 1, 2, 3 and to 4.

6. An expression vector comprising the polynucleotide according to claim 5.

7. A recombinant host cell transformed with the expression vector according to claim 6.

8. A method of producing an antibody or antigen-binding fragment thereof comprising:
   culturing the recombinant host cell according to claim 7 to produce an antibody or an antigen-binding fragment thereof; and
   recovering the produced antibody or antigen-binding fragment thereof, followed by isolation and purification.

9. A column for isolating or purifying a recombinant coagulation factor VIII,
   wherein the antibody or antigen-binding fragment thereof according to claim 1 as a ligand for isolating or purifying the recombinant coagulation factor VIII is coupled to a stationary phase of the column.

10. A method of isolating or purifying a recombinant coagulation factor VIII comprising loading a sample containing a recombinant coagulation factor VIII on the column according to claim 9.

* * * * *

UNITED STATES PATENT AND TRADEMARK OFFICE
CERTIFICATE OF CORRECTION

Page 1 of 1

PATENT NO. : 11,155,635 B2
APPLICATION NO. : 16/464287
DATED : October 26, 2021
INVENTOR(S) : Jaeseung Yoon et al.

It is certified that error appears in the above-identified patent and that said Letters Patent is hereby corrected as shown below:

In the Specification

Column 8, Line 45, "ipp promoter, pLX promoter, pRX promoter" should be -- lpp promoter, pLλ promoter, pRλ promoter --.

Column 8, Line 51, "R-actin" should be -- β-actin --.

In the Claims

Column 46, Line 3, "and to 4" should be -- and 4 --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: VH CDR1

<400> SEQUENCE: 1

Gly Phe Thr Phe Ser Asp Ala Trp Met Asp
1               5                   10

<210> SEQ ID NO 2
<211> LENGTH: 19
<212> TYPE: PRT
<213> ORGANISM: Artificial Sequence
<220> FEATURE:
<223> OTHER INFORMATION: VH CDR2

<400> SEQUENCE: 2

Glu Ile Arg Ser Lys Ala Lys Asn His Ala Thr Asn Tyr Ala Glu Ser
1               5                   10                  15

Val Lys Gly

<210> SEQ ID NO 3
<211> LENGTH: 17
<212> TYPE: PRT
<213> ORGANISM: Artificial Sequence
<220> FEATURE:
<223> OTHER INFORMATION: VL CDR1

<400> SEQUENCE: 3

Lys Ser Ser Gln Ser Leu Leu Asn Ser Ile Asn Gln Glu Asn Tyr Leu
1               5                   10                  15

Ala

<210> SEQ ID NO 4
<211> LENGTH: 7
<212> TYPE: PRT
<213> ORGANISM: Artificial Sequence
<220> FEATURE:
<223> OTHER INFORMATION: VL CDR2

<400> SEQUENCE: 4

Phe Gly Ser Thr Arg Glu Ser
1               5

<210> SEQ ID NO 5
<211> LENGTH: 9
<212> TYPE: PRT
<213> ORGANISM: Artificial Sequence
<220> FEATURE:
<223> OTHER INFORMATION: VL CDR3

<400> SEQUENCE: 5

Gln Gln His Tyr Ser Thr Pro Tyr Thr
1               5

<210> SEQ ID NO 6
<211> LENGTH: 30
```

```
<212> TYPE: PRT
<213> ORGANISM: Artificial Sequence
<220> FEATURE:
<223> OTHER INFORMATION: VH FR1

<400> SEQUENCE: 6

Glu Val Lys Ile Glu Glu Ser Gly Gly Gly Leu Val Gln Pro Gly Gly
1               5                   10                  15

Ser Met Lys Leu Ser Cys Ala Ala Ser Gly Phe Thr Phe Ser
            20                  25                  30

<210> SEQ ID NO 7
<211> LENGTH: 14
<212> TYPE: PRT
<213> ORGANISM: Artificial Sequence
<220> FEATURE:
<223> OTHER INFORMATION: VH FR2

<400> SEQUENCE: 7

Trp Val Arg Gln Ser Pro Glu Lys Gly Leu Glu Trp Val Ala
1               5                   10

<210> SEQ ID NO 8
<211> LENGTH: 39
<212> TYPE: PRT
<213> ORGANISM: Artificial Sequence
<220> FEATURE:
<223> OTHER INFORMATION: VH FR3

<400> SEQUENCE: 8

Tyr Ala Glu Ser Val Lys Gly Arg Phe Thr Ile Ser Arg Asp Asp Ser
1               5                   10                  15

Lys Ser Arg Val Tyr Leu Gln Met Asn Thr Leu Arg Ala Glu Asp Thr
            20                  25                  30

Gly Ile Tyr Tyr Cys Thr Asn
        35

<210> SEQ ID NO 9
<211> LENGTH: 11
<212> TYPE: PRT
<213> ORGANISM: Artificial Sequence
<220> FEATURE:
<223> OTHER INFORMATION: VH FR4

<400> SEQUENCE: 9

Trp Gly Pro Gly Thr Thr Leu Thr Val Ser Ser
1               5                   10

<210> SEQ ID NO 10
<211> LENGTH: 23
<212> TYPE: PRT
<213> ORGANISM: Artificial Sequence
<220> FEATURE:
<223> OTHER INFORMATION: VL FR1

<400> SEQUENCE: 10

Asp Ile Val Met Thr Gln Ser Pro Ser Ser Leu Ala Met Ser Val Gly
1               5                   10                  15

Gln Lys Val Thr Met Ser Cys
            20

<210> SEQ ID NO 11
<211> LENGTH: 15
<212> TYPE: PRT
<213> ORGANISM: Artificial Sequence
```

```
<220> FEATURE:
<223> OTHER INFORMATION: VL FR2

<400> SEQUENCE: 11

Trp Tyr Gln Gln Lys Pro Gly Gln Ser Pro Lys Leu Leu Ile Tyr
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: VL FR3

<400> SEQUENCE: 12

Gly Val Pro Asp Arg Phe Ile Gly Ser Gly Ser Gly Thr Asp Phe Ser
1               5                   10                  15

Leu Thr Ile Ser Asp Val Gln Ala Glu Asp Leu Ala Asp Tyr Phe Cys
            20                  25                  30

<210> SEQ ID NO 13
<211> LENGTH: 12
<212> TYPE: PRT
<213> ORGANISM: Artificial Sequence
<220> FEATURE:
<223> OTHER INFORMATION: VL FR4

<400> SEQUENCE: 13

Phe Gly Gly Gly Thr Lys Leu Glu Met Lys Arg Ala
1               5                   10

<210> SEQ ID NO 14
<211> LENGTH: 114
<212> TYPE: PRT
<213> ORGANISM: Artificial Sequence
<220> FEATURE:
<223> OTHER INFORMATION: VH

<400> SEQUENCE: 14

Glu Val Lys Ile Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Lys Asn His Ala Thr Asn Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Thr Leu Arg Ala Glu Asp Thr Gly Ile Tyr
                85                  90                  95

Tyr Cys Thr Asn Tyr His Phe Trp Gly Pro Gly Thr Thr Leu Thr Val
            100                 105                 110

Ser Ser

<210> SEQ ID NO 15
<211> LENGTH: 115
<212> TYPE: PRT
<213> ORGANISM: Artificial Sequence
<220> FEATURE:
<223> OTHER INFORMATION: VL

<400> SEQUENCE: 15
```

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ile Asn Gln Glu Asn Tyr Leu Ala Trp Tyr Gln Lys Pro Gly Gln
        35                  40                  45

Ser Pro Lys Leu Leu Ile Tyr Phe Gly Ser Thr Arg Glu Ser Gly Val
    50                  55                  60

Pro Asp Arg Phe Ile Gly Ser Gly Ser Gly Thr Asp Phe Ser Leu Thr
65                  70                  75                  80

Ile Ser Asp Val Gln Ala Glu Asp Leu Ala Asp Tyr Phe Cys Gln Gln
                85                  90                  95

His Tyr Ser Thr Pro Tyr Thr Phe Gly Gly Gly Thr Lys Leu Glu Met
            100                 105                 110

Lys Arg Ala
        115
```

<210> SEQ ID NO 16
<211> LENGTH: 438
<212> TYPE: PRT
<213> ORGANISM: Artificial Sequence
<220> FEATURE:
<223> OTHER INFORMATION: Heavy Chain

<400> SEQUENCE: 16

```
Glu Val Lys Ile Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Lys Asn His Ala Thr Asn Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Asn Thr Leu Arg Ala Glu Asp Thr Gly Ile Tyr
                85                  90                  95

Tyr Cys Thr Asn Tyr His Phe Trp Gly Pro Gly Thr Thr Leu Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240
```

```
Val Leu Thr Ile Thr Leu Thr Pro Lys Val Thr Cys Val Val Asp
            245                 250                 255

Ile Ser Lys Asp Asp Pro Glu Val Gln Phe Ser Trp Phe Val Asp Asp
                260                 265                 270

Val Glu Val His Thr Ala Gln Thr Gln Pro Arg Glu Glu Gln Phe Asn
            275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asp Phe Phe Pro Glu Asp Ile
                355                 360                 365

Thr Val Glu Trp Gln Trp Asn Gly Gln Pro Ala Glu Asn Tyr Lys Asn
            370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
            435

<210> SEQ ID NO 17
<211> LENGTH: 220
<212> TYPE: PRT
<213> ORGANISM: Artificial Sequence
<220> FEATURE:
<223> OTHER INFORMATION: Light Chain

<400> SEQUENCE: 17

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ile Asn Gln Glu Asn Tyr Leu Ala Trp Tyr Gln Gln Lys Pro Gly Gln
        35                  40                  45

Ser Pro Lys Leu Leu Ile Tyr Phe Gly Ser Thr Arg Glu Ser Gly Val
    50                  55                  60

Pro Asp Arg Phe Ile Gly Ser Gly Ser Gly Thr Asp Phe Ser Leu Thr
65                  70                  75                  80

Ile Ser Asp Val Gln Ala Glu Asp Leu Ala Asp Tyr Phe Cys Gln Gln
                85                  90                  95

His Tyr Ser Thr Pro Tyr Thr Phe Gly Gly Gly Thr Lys Leu Glu Met
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160
```

```
Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 18
<211> LENGTH: 1438
<212> TYPE: PRT
<213> ORGANISM: Artificial Sequence
<220> FEATURE:
<223> OTHER INFORMATION: Recombinant Blood Coagulation Factor VIII

<400> SEQUENCE: 18

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300
```

```
Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
            325                 330                 335

Met Lys Asn Asn Glu Glu Ala Glu Asp Tyr Asp Asp Leu Thr Asp
        340                 345                 350

Ser Glu Met Asp Val Val Arg Phe Asp Asp Asn Ser Pro Ser Phe
    355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720
```

-continued

```
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Pro Val Leu Lys Arg His
            740                 745                 750
Gln Arg Glu Ile Thr Arg Thr Thr Leu Gln Ser Asp Gln Glu Glu Ile
        755                 760                 765
Asp Tyr Asp Asp Thr Ile Ser Val Glu Met Lys Lys Glu Asp Phe Asp
    770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
                835                 840                 845
Phe Thr Gln Pro Leu Tyr Arg Gly Glu Leu Asn Glu His Leu Gly Leu
    850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
                915                 920                 925
Met Ala Pro Thr Lys Asp Glu Phe Asp Cys Lys Ala Trp Ala Tyr Phe
            930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
                980                 985                 990
Lys Ser Trp Tyr Phe Thr Glu Asn Met Glu Arg Asn Cys Arg Ala Pro
        995                 1000                1005
Cys Asn Ile Gln Met Glu Asp Pro Thr Phe Lys Glu Asn Tyr Arg
    1010                1015                1020
Phe His Ala Ile Asn Gly Tyr Ile Met Asp Thr Leu Pro Gly Leu
    1025                1030                1035
Val Met Ala Gln Asp Gln Arg Ile Arg Trp Tyr Leu Leu Ser Met
    1040                1045                1050
Gly Ser Asn Glu Asn Ile His Ser Ile His Phe Ser Gly His Val
    1055                1060                1065
Phe Thr Val Arg Lys Lys Glu Glu Tyr Lys Met Ala Leu Tyr Asn
    1070                1075                1080
Leu Tyr Pro Gly Val Phe Glu Thr Val Glu Met Leu Pro Ser Lys
    1085                1090                1095
Ala Gly Ile Trp Arg Val Glu Cys Leu Ile Gly Glu His Leu His
    1100                1105                1110
Ala Gly Met Ser Thr Leu Phe Leu Val Tyr Ser Asn Lys Cys Gln
    1115                1120                1125
Thr Pro Leu Gly Met Ala Ser Gly His Ile Arg Asp Phe Gln Ile
```

| | | | | | | | | |
|---|---|---|---|---|---|---|---|---|
| | | 1130 | | | 1135 | | | 1140 |

Thr Ala Ser Gly Gln Tyr Gly Gln Trp Ala Pro Lys Leu Ala Arg
     1145               1150               1155

Leu His Tyr Ser Gly Ser Ile Asn Ala Trp Ser Thr Lys Glu Pro
     1160               1165               1170

Phe Ser Trp Ile Lys Val Asp Leu Leu Ala Pro Met Ile Ile His
     1175               1180               1185

Gly Ile Lys Thr Gln Gly Ala Arg Gln Lys Phe Ser Ser Leu Tyr
     1190               1195               1200

Ile Ser Gln Phe Ile Ile Met Tyr Ser Leu Asp Gly Lys Lys Trp
     1205               1210               1215

Gln Thr Tyr Arg Gly Asn Ser Thr Gly Thr Leu Met Val Phe Phe
     1220               1225               1230

Gly Asn Val Asp Ser Ser Gly Ile Lys His Asn Ile Phe Asn Pro
     1235               1240               1245

Pro Ile Ile Ala Arg Tyr Ile Arg Leu His Pro Thr His Tyr Ser
     1250               1255               1260

Ile Arg Ser Thr Leu Arg Met Glu Leu Met Gly Cys Asp Leu Asn
     1265               1270               1275

Ser Cys Ser Met Pro Leu Gly Met Glu Ser Lys Ala Ile Ser Asp
     1280               1285               1290

Ala Gln Ile Thr Ala Ser Ser Tyr Phe Thr Asn Met Phe Ala Thr
     1295               1300               1305

Trp Ser Pro Ser Lys Ala Arg Leu His Leu Gln Gly Arg Ser Asn
     1310               1315               1320

Ala Trp Arg Pro Gln Val Asn Asn Pro Lys Glu Trp Leu Gln Val
     1325               1330               1335

Asp Phe Gln Lys Thr Met Lys Val Thr Gly Val Thr Thr Gln Gly
     1340               1345               1350

Val Lys Ser Leu Leu Thr Ser Met Tyr Val Lys Glu Phe Leu Ile
     1355               1360               1365

Ser Ser Ser Gln Asp Gly His Gln Trp Thr Leu Phe Phe Gln Asn
     1370               1375               1380

Gly Lys Val Lys Val Phe Gln Gly Asn Gln Asp Ser Phe Thr Pro
     1385               1390               1395

Val Val Asn Ser Leu Asp Pro Pro Leu Leu Thr Arg Tyr Leu Arg
     1400               1405               1410

Ile His Pro Gln Ser Trp Val His Gln Ile Ala Leu Arg Met Glu
     1415               1420               1425

Val Leu Gly Cys Glu Ala Gln Asp Leu Tyr
     1430               1435

<210> SEQ ID NO 19
<211> LENGTH: 399
<212> TYPE: DNA
<213> ORGANISM: Artificial Sequence
<220> FEATURE:
<223> OTHER INFORMATION: VH coding nucleotide

<400> SEQUENCE: 19

| | | | | |
|---|---|---|---|---|
| atgtacttgg | gactgaacta | tgtattcata | gttttttctct | taaatggtgt | ccagagtgaa | 60 |
| gtgaagattg | aggagtctgg | aggaggcttg | gtgcagcctg | gaggatccat | gaaactctct | 120 |
| tgtgctgcct | ctggattcac | ttttagtgac | gcctggatgg | actgggtccg | ccagtctcca | 180 |
| gagaagggtc | ttgagtgggt | tgctgaaatt | agaagcaaag | ctaaaaatca | tgcaacaaac | 240 |

```
tatgctgagt ctgtgaaagg gaggttcacc atctcaagag atgattccaa aagtcgtgtc    300
tacctgcaaa tgaacacctt aagagctgaa gacactggca tttattactg taccaattac    360
cacttctggg gcccaggcac cactctcaca gtctcctca                           399
```

```
<210> SEQ ID NO 20
<211> LENGTH: 417
<212> TYPE: DNA
<213> ORGANISM: Artificial Sequence
<220> FEATURE:
<223> OTHER INFORMATION: VL coding nucleotide

<400> SEQUENCE: 20
atgggcatca agatggagtc acattttcag gtcctcatgt ttcttctgct ctgggtatct     60
ggtgcctgtg cagacattgt gatgacacag tctccatcct ccctggctat gtcagtagga    120
cagaaggtca ctatgagctg caagtccagt cagagtcttt aaatagtat caatcaagag     180 aactatttgg cctggtacca gcagaaacca ggacagtctc ctaaacttct gatatacttt    240
ggatccacta gggaatctgg ggtccctgat cgcttcatag gcagtggatc tgggacagat    300
ttctctctta ccattagtga cgtgcaggct gaagacctgg cagattactt ctgtcagcaa    360
cattatagta ctccgtacac gttcggaggg gggaccaagc tagaaatgaa acgggct      417
```

```
<210> SEQ ID NO 21
<211> LENGTH: 1374
<212> TYPE: DNA
<213> ORGANISM: Artificial Sequence
<220> FEATURE:
<223> OTHER INFORMATION: Heavy Chain coding nucleotide

<400> SEQUENCE: 21
atgtacttgg gactgaacta tgtattcata gtttttctct taaatggtgt ccagagtgaa     60
gtgaagattg aggagtctgg aggaggcttg gtgcagcctg gaggatccat gaaactctct    120
tgtgctgcct ctggattcac ttttagtgac gcctggatgg actgggtccg ccagtctcca    180
gagaagggtc ttgagtgggt tgctgaaatt agaagcaaag ctaaaaatca tgcaacaaac    240
tatgctgagt ctgtgaaagg gaggttcacc atctcaagag atgattccaa aagtcgtgtc    300
tacctgcaaa tgaacacctt aagagctgaa gacactggca tttattactg taccaattac    360
cacttctggg gcccaggcac cactctcaca gtctcctcag ccaaaacgac ccccatct     420 gtctatccac tggcccctgg atctgctgcc caaactaact ccatggtgac cctgggatgc    480
ctggtcaagg gctatttccc tgagccagtg acagtgacct ggaactctgg atccctgtcc    540
agcggtgtgc acaccttccc agctgtcctg cagtctgacc tctacactct gagcagctca    600
gtgactgtcc cctccagcac ctggcccagc gagaccgtca cctgcaacgt tgcccacccg    660
gccagcagca ccaaggtgga caagaaaatt gtgcccaggg attgtggttg taagccttgc    720
atatgtacag tcccagaagt atcatctgtc ttcatcttcc ccccaaagcc caaggatgtg    780
ctcaccatta ctctgactcc taaggtcacg tgtgttgtgg tagacatcag caaggatgat    840
cccgaggtcc agttcagctg gtttgtagat gatgtggagg tgcacacagc tcagacgcaa    900
ccccgggagg agcagttcaa cagcactttc cgctcagtca gtgaacttcc catcatgcac    960
caggactggc tcaatggcaa ggagttcaaa tgcagggtca acagtgcagc tttccctgcc   1020
cccatcgaga aaaccatctc caaaaccaaa ggcagaccga aggctccaca ggtgtacacc   1080
attccacctc caaggagca gatggccaag gataaagtca gtctgacctg catgataaca   1140
```

```
gacttcttcc ctgaagacat tactgtggag tggcagtgga atgggcagcc agcggagaac    1200
tacaagaaca ctcagcccat catggacaca gatggctctt acttcgtcta cagcaagctc    1260
aatgtgcaga agagcaactg ggaggcagga aatactttca cctgctctgt gttacatgag    1320
ggcctgcaca accaccatac tgagaagagc ctctcccact ctcctggtaa atga          1374

<210> SEQ ID NO 22
<211> LENGTH: 735
<212> TYPE: DNA
<213> ORGANISM: Artificial Sequence
<220> FEATURE:
<223> OTHER INFORMATION: Light Chain coding nucleotide

<400> SEQUENCE: 22
atgggcatca agatggagtc acattttcag gtcctcatgt ttcttctgct ctgggtatct      60
ggtgcctgtg cagacattgt gatgacacag tctccatcct ccctggctat gtcagtagga    120
cagaaggtca ctatgagctg caagtccagt cagagtcttt aaatagtat caatcaagag     180 aactatttgg cctggtacca gcagaaacca ggacagtctc ctaaacttct gatatacttt    240
ggatccacta gggaatctgg ggtccctgat cgcttcatag gcagtggatc tgggacagat    300
ttctctctta ccattagtga cgtgcaggct gaagacctgg cagattactt ctgtcagcaa    360
cattatagta ctccgtacac gttcggaggg gggaccaagc tagaaatgaa acgggctgat    420
gctgcaccaa ctgtatccat cttcccacca tccagtgagc agttaacatc tggaggtgcc    480
tcagtcgtgt gcttcttgaa caacttctac cccaaagaca tcaatgtcaa gtggaagatt    540
gatggcagtg aacggcaaaa tggcgtcctg aacagttgga ctgatcagga cagcaaagac    600
agcacctaca gcatgagcag caccctcacg ttgaccaagg acgagtatga acgacataac    660
agctatacct gtgaggccac tcacaagaca tcaacttcac ccattgtcaa gagcttcaac    720
aggaatgagt gttag                                                     735

<210> SEQ ID NO 23
<211> LENGTH: 21
<212> TYPE: DNA
<213> ORGANISM: Artificial Sequence
<220> FEATURE:
<223> OTHER INFORMATION: GSP1 Primer

<400> SEQUENCE: 23
tgaggagacg gtgaccgtgg t                                               21

<210> SEQ ID NO 24
<211> LENGTH: 21
<212> TYPE: DNA
<213> ORGANISM: Artificial Sequence
<220> FEATURE:
<223> OTHER INFORMATION: GSP2 Primer

<400> SEQUENCE: 24
ccttggcccc agaagtggta a                                               21

<210> SEQ ID NO 25
<211> LENGTH: 20
<212> TYPE: DNA
<213> ORGANISM: Artificial Sequence
<220> FEATURE:
<223> OTHER INFORMATION: Nested Primer

<400> SEQUENCE: 25
taaatgccag tgtcttcagc                                                 20
```

<210> SEQ ID NO 26
<211> LENGTH: 42
<212> TYPE: DNA
<213> ORGANISM: Artificial Sequence
<220> FEATURE:
<223> OTHER INFORMATION: MKV1 Primer

<400> SEQUENCE: 26
gctagcgcca ccatgaagtt gcctgttagg ctgttggtgc tg                42

<210> SEQ ID NO 27
<211> LENGTH: 42
<212> TYPE: DNA
<213> ORGANISM: Artificial Sequence
<220> FEATURE:
<223> OTHER INFORMATION: MKV2 Primer

<400> SEQUENCE: 27
gctagcgcca ccatggagwc agacacactc ctgytatggg tg                42

<210> SEQ ID NO 28
<211> LENGTH: 42
<212> TYPE: DNA
<213> ORGANISM: Artificial Sequence
<220> FEATURE:
<223> OTHER INFORMATION: MKV3 Primer

<400> SEQUENCE: 28
gctagcgcca ccatgagtgt gctcactcag gtcctggsgt tg                42

<210> SEQ ID NO 29
<211> LENGTH: 42
<212> TYPE: DNA
<213> ORGANISM: Artificial Sequence
<220> FEATURE:
<223> OTHER INFORMATION: MKV4 Primer

<400> SEQUENCE: 29
gctagcgcca ccatgaggrc ccctgctcag wttyttggmw tc                42

<210> SEQ ID NO 30
<211> LENGTH: 42
<212> TYPE: DNA
<213> ORGANISM: Artificial Sequence
<220> FEATURE:
<223> OTHER INFORMATION: MKV5 Primer

<400> SEQUENCE: 30
gctagcgcca ccatggattt wcaggtgcag attwtcagct tc                42

<210> SEQ ID NO 31
<211> LENGTH: 39
<212> TYPE: DNA
<213> ORGANISM: Artificial Sequence
<220> FEATURE:
<223> OTHER INFORMATION: MKV6 Primer

<400> SEQUENCE: 31
gctagcgcca ccatgaggtk cyytgytsag ytyctgrgg                    39

<210> SEQ ID NO 32
<211> LENGTH: 43
<212> TYPE: DNA
<213> ORGANISM: Artificial Sequence
<220> FEATURE:

<223> OTHER INFORMATION: MKV7 Primer

<400> SEQUENCE: 32
gctagcgcca ccatgggcwt caagatggag tcacakwyyc wgg     43

<210> SEQ ID NO 33
<211> LENGTH: 43
<212> TYPE: DNA
<213> ORGANISM: Artificial Sequence
<220> FEATURE:
<223> OTHER INFORMATION: MKV8 Primer

<400> SEQUENCE: 33
gctagcgcca ccatgtgggg ayctktttyc mmtttttcaa ttg     43

<210> SEQ ID NO 34
<211> LENGTH: 37
<212> TYPE: DNA
<213> ORGANISM: Artificial Sequence
<220> FEATURE:
<223> OTHER INFORMATION: MKV9 Primer

<400> SEQUENCE: 34
gctagcgcca ccatggtrtc cwcasctcag ttccttg     37

<210> SEQ ID NO 35
<211> LENGTH: 39
<212> TYPE: DNA
<213> ORGANISM: Artificial Sequence
<220> FEATURE:
<223> OTHER INFORMATION: MKV10 Primer

<400> SEQUENCE: 35
gctagcgcca ccatgtatat atgtttgttg tctatttct     39

<210> SEQ ID NO 36
<211> LENGTH: 40
<212> TYPE: DNA
<213> ORGANISM: Artificial Sequence
<220> FEATURE:
<223> OTHER INFORMATION: MKV11 Primer

<400> SEQUENCE: 36
gctagcgcca ccatggaagc cccagctcag cttctcttcc     40

<210> SEQ ID NO 37
<211> LENGTH: 25
<212> TYPE: DNA
<213> ORGANISM: Artificial Sequence
<220> FEATURE:
<223> OTHER INFORMATION: MKCIII Primer

<400> SEQUENCE: 37
ctaacactca ttcctgttga agctc     25